United States Patent
Suh et al.

(10) Patent No.: US 7,939,663 B2
(45) Date of Patent: May 10, 2011

(54) METALLIC COMPOUND AND ORGANIC ELECTROLUMINESCENCE DEVICE COMPRISING THE SAME

(75) Inventors: Dong-Hack Suh, Seongnam (KR); Jin-Soo Lim, Seoul (KR); Ji-Ho Kim, Seoul (KR); Sun-Hyun Choi, Suncheon (KR)

(73) Assignees: Samsung Electronics Co., Ltd. (KR); Industry-University Cooperation Foundation, Hanyang University (KR)

( * ) Notice: Subject to any disclaimer, the term of this patent is extended or adjusted under 35 U.S.C. 154(b) by 276 days.

(21) Appl. No.: 11/913,243

(22) PCT Filed: Jan. 8, 2007

(86) PCT No.: PCT/KR2007/000110
§ 371 (c)(1),
(2), (4) Date: Oct. 31, 2007

(87) PCT Pub. No.: WO2007/078181
PCT Pub. Date: Jul. 12, 2007

(65) Prior Publication Data
US 2008/0275239 A1  Nov. 6, 2008

(30) Foreign Application Priority Data

Jan. 6, 2006  (KR) .................. 10-2006-0001777

(51) Int. Cl.
*C07F 15/00* (2006.01)
*H01L 51/50* (2006.01)
(52) U.S. Cl. .......... 546/10; 428/690; 313/504; 548/108
(58) Field of Classification Search ............... 546/10; 428/690; 313/504; 548/108
See application file for complete search history.

(56) References Cited

U.S. PATENT DOCUMENTS

| 6,703,146 | B1 | 3/2004 | Sakaguchi et al. |
| 2005/0287391 | A1 | 12/2005 | Chang et al. |

FOREIGN PATENT DOCUMENTS

| JP | 2003264086 | 9/2003 |
| JP | 2004158391 | 6/2004 |
| JP | 2005226066 | 8/2005 |

OTHER PUBLICATIONS

International Search Report; PCT/KR2007/000110; Apr. 11, 2007. All references cited in the Search Report and not previously submitted are listed above.
Synthesis and Characterization of Phosphorescent Cyclometalated Iridium Complexes; Sergey Lamansky, Peter Djurovich, Drew Murphy, Feras Abdel-Razzaq, Raymond Kwong, Irina Tsyba, Manfred Bortz, Becky Mui, Robert Bau, and Mark E. Thompson; Imorg. Chem. 2001, 40, 1704-1711.
New, efficient electroluminescent materials based on organometallic Ir complexes; Vladimir V. Grushin,, Norman Herron, Daniel D. LeCloux, William J. Marshall, Viacheslav A. Petrov and Ying Wang; Chem. Commun. 2001, 1494-1495.
Written Opinion International Searching Authority; PCT/KR2007/000110; Apr. 11, 2007. All references cited in the Opinion and not previously submitted are listed above.
'Highly Phosphorescent Bis-Cyclometalated Iridium Complexes; Synthesis, Photophysical Characterization, and Use in Organic Light Emitting Diodes'; Sergey Lamansky, Peter Djurovich, Drew Murphy, Feras Abdel-Razzaq, Hae-Eun Lee, Chihaya Adachi, Paul E. Burrows, Stephen R. Forrest, and Mark E. Thompson; J. Am. Chem. Soc. 2001, vol. 123, No. 18, pp. 4304-4312.

*Primary Examiner* — Charanjit S Aulakh
(74) *Attorney, Agent, or Firm* — Cantor Colburn LLP

(57) ABSTRACT

The present invention relates to a light emitting transition metal compound represented by the Chemical Formula 1 and Chemical Formula 2 and an organic electroluminescence device including the same. In the above Chemical Formulae 1 and 2, M is Ir, Pt, Rh, Re, Os, or the like, m is 2 or 3 and n is 0 or 1, where the sum of m and n is 3, provided that the sum of m and n is 2 when M is Pt, X and Z are the same or different and may be N or P, and Y is O, S, or Se.

4 Claims, No Drawings

METALLIC COMPOUND AND ORGANIC ELECTROLUMINESCENCE DEVICE COMPRISING THE SAME

TECHNICAL FIELD

The present invention relates to a metallic compound and an organic electroluminescence device including the same, and more particularly, to a metallic compound that is applicable as a highly efficient phosphor host material and an organic electroluminescence device including the same.

BACKGROUND OF ART

An electroluminescence device (EL device) is a self-light emitting display device having such merits as a wide viewing angle and excellent contrast as well as a quick response time.

EL devices are classified into an inorganic EL device and an organic EL device in accordance with a material used for a light emitting layer. The organic EL device has merits of improved luminance, driving voltage, response speed, and multi-colorfying property compared to an inorganic EL device.

An organic EL device is generally composed of an anode on a substrate, a hole transport layer on the anode, and a light emitting layer, an electron transport layer (ETL), and a cathode sequentially positioned thereon. The hole transport layer, light emitting layer, and electron transport layer (ETL) are organic films that are composed of organic compounds.

The organic EL device having the above structure is operated as follows.

When a voltage is applied to a space between the anode and the cathode, the holes are injected from the anode to the light emitting layer through the hole transport layer. Meanwhile, when the electrons are injected from the cathode into the light emitting layer through the electron transport layer (ETL), carriers are recombined in the region of the light emitting layer to thereby produce excitons. The state of the excitons is changed from an exited state to a base state, and the change in the state of the excitons makes the molecules of the light emitting layer emit light to thereby form an image.

Materials for forming a light emitting layer are divided into fluorescent materials using singlet excitons and phosphorescent materials using triplet excitons according to the light emitting mechanism. Phosphorescent materials generally include organic/inorganic compound structures including transition metal atoms. The transition metal atoms change triplet excitons, which used to be impossible to transition, into excitons that are possible to transition, causing them to emit phosphorescent light. Since the phosphorescent materials can use triplet excitons having a generation probability of 75%, higher luminous efficiency can be achieved than with fluorescent materials using singlet excitons having a generation probability of 25%.

Among light emitting materials using the triplet excitons are phosphorescent materials including iridium and platinum compounds (Sergey Lamansky et al. Inorg. Chem., 40, 1704-1711, 2001, and Sergey Lamansky et al., J. Am. Chem. Soc., 123, 4304-4312, 2001). For blue light emitting materials, Ir compounds based on (4,6-F2 ppy)$_2$Irpic or a fluorinated ppy ligand structure have been developed (Vladimir V. Grushin et al., Chem. Commun., 1494-1495, 2001). The (4,6-F2 ppy)$_2$Irpic, however, has shortcomings that it emits light in a sky blue region and its large shoulder peaks increase a y value in color purity coordinates. Researchers are studying red and green light emitting materials, but there still remains great demand to develop highly efficient phosphorescent materials having a long lifespan.

DETAILED DESCRIPTION OF THE INVENTION

Technical Problem

In order to solve the problems, the object of the present invention is to provide a phosphor metallic compound having a new ligand structure, and an organic electroluminescence device having improved luminous efficiency and color purity.

Technical Solution

The present invention relates to a light emitting transition metal compound represented by the following Chemical Formula 1 and Chemical Formula 2, and an organic electroluminescence device including the same.

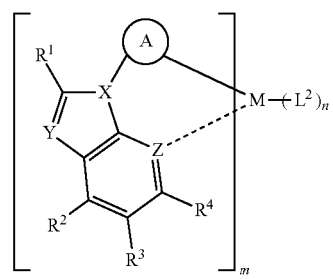

[Chemical Formula 1]

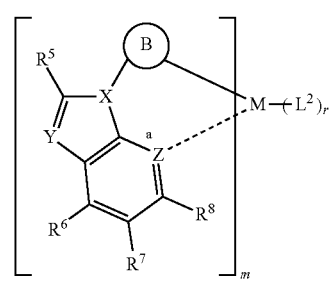

[Chemical Formula 2]

In the above Chemical Formulae 1 and 2, M is Ir, Pt, Rh, Re, Os, or the like, m is 2 or 3, n is 0 or 1, with the sum of m and n being 3, provided that the sum of m and n is 2 when M is Pt, X and Z are the same or different and may be N or P, and Y is O, S, or Se.

A of Chemical Formula 1 is represented by any one of the following Chemical Formulae 3:

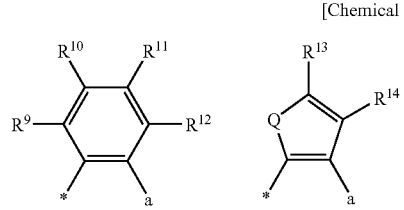

[Chemical Formulae 3]

-continued

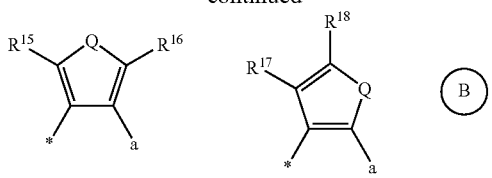

of Chemical Formula 2 is represented by any one of the following Chemical Formulae 4:

[Chemical Formulae 4]

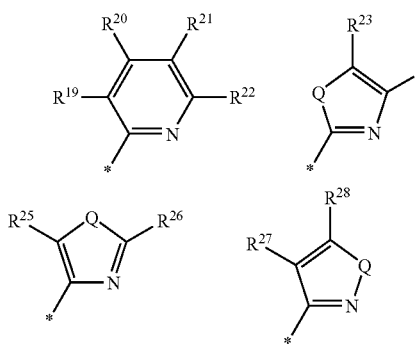

In the above Chemical Formulae 3 and 4, Q is O, S, or Se. In the above Chemical Formulae 3 and 4, * denotes a portion that is covalently bound with X, and the transition metal M of the above Chemical Formula 1 forms a complex compound while bound with a portion denoted as "a" in the above Chemical Formulae 3 by a covalent bond and bound with Z of Chemical Formula 1 by a coordination bond. In the above Chemical Formula 2, the transition metal M forms a complex compound while bound with an N atom of the above Chemical Formulae 4 by a coordination bond and with a portion denoted as "a" in the above Chemical Formula 2 by a covalent bond. In the above Chemical Formulae 1 and 2, $R^2$, $R^3$, $R^4$, $R^6$, $R^7$, and $R^8$ are hydrogen, a C1 to C20 alkyl, an aryl, a cycloalkyl, a halogen, a linear or branched substituent including at least one halogen, a linear or branched substituent including at least one heteroatom, carbonyl, vinyl, or acetylenyl, or may form a cycle, and they may be the same or different. $R^1$ and $R^5$ are hydrogen, a C1 to C7 alkyl excluding an aromatic cyclic substituent, a cycloalkyl, a halogen, a linear or branched substituent including at least one halogen, or a linear or branched substituent including at least one heteroatom.

In the above Chemical Formulae 1 and 2, $L^2$ is represented by the following Chemical Formulae 5, 6, and 7.

[Chemical Formulae 5]

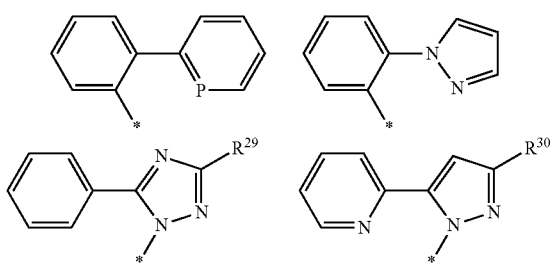

-continued

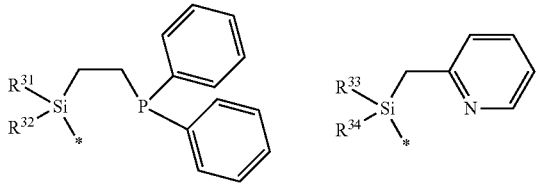

[Chemical Formula 6]

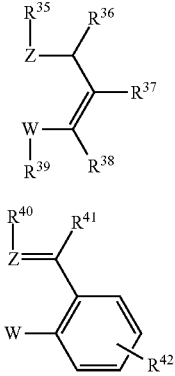

[Chemical Formula 7]

In the above Chemical Formulae 1 and 2, the transition metal M forms a complex compound by a covalent bond with a portion denoted as * in the above Chemical Formulae 5, and a coordination bond with an adjacent N or P atom.

Z and W in the above Chemical Formulae 6 and 7 are the same or different, and may be a heteroatom of O, N, S, or P, $R^{29}$-$R^{42}$ in the Chemical Formulae 5, 6, and 7 are the same or different, and may be hydrogen, a C1 to C20 alkyl, an aryl, cycloalkyl, halogen, a linear or branched substituent including at least one halogen, a linear or branched substituent including at least one heteroatom, carbonyl, vinyl, or acetylenyl, or may form a cycle.

In the present invention, a ligand of the transition metal compound includes an N-arylbenzo oxazole-based derivative and an N-arylbenzo thiazole-based derivative including a transition metal having a covalent bond with C and a coordination bond with N. In order to reduce concentration quenching, a functional group having a large steric hindrance, such as an alkyl, an aryl, a halogen, a silyl, and so on, is independently included in benzooxazole or benzothiazole, and an aryl. Several nm of light-emission and light wavelength can be easily controlled in accordance with the positions of the substituents and the properties of electron donors or acceptors. The ligands of the present invention are represented by any one of the following Chemical Formulae 8.

[Chemical Formulae 8]

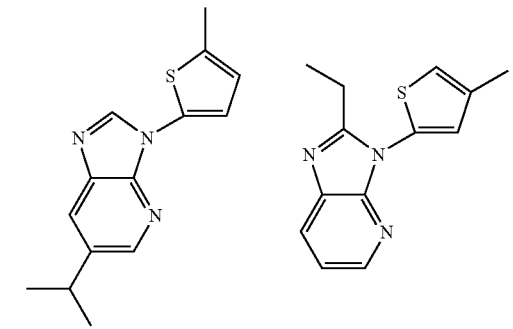

-continued
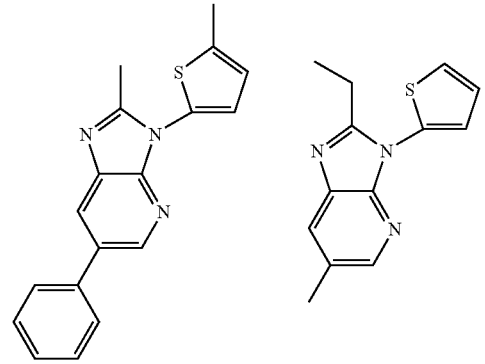
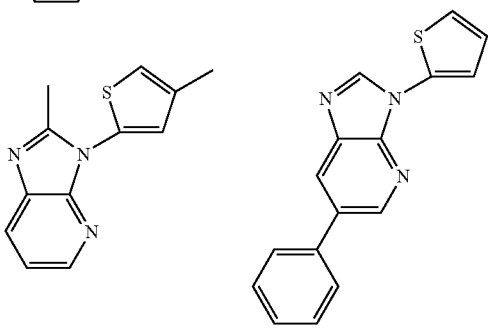
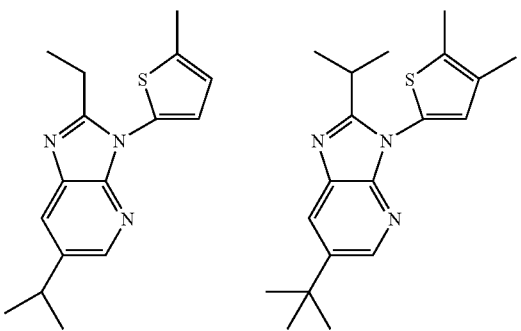
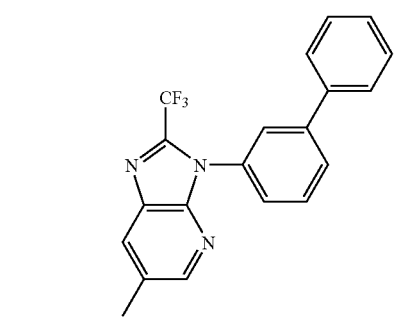
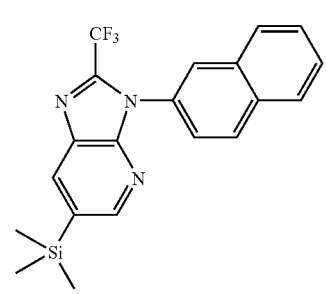
-continued
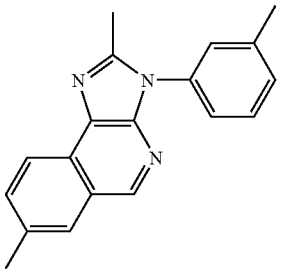
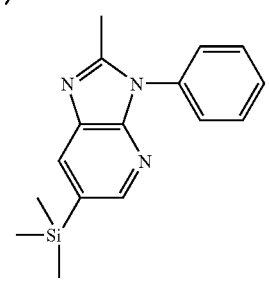
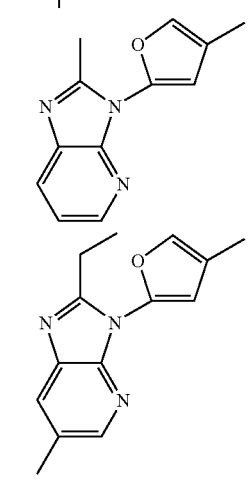
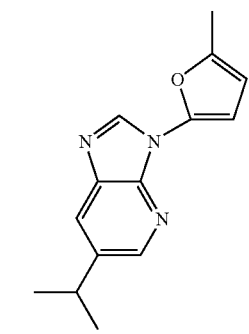
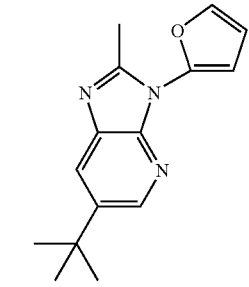

-continued
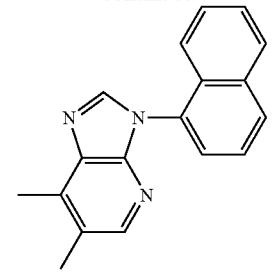
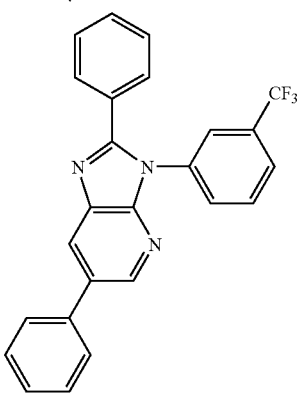
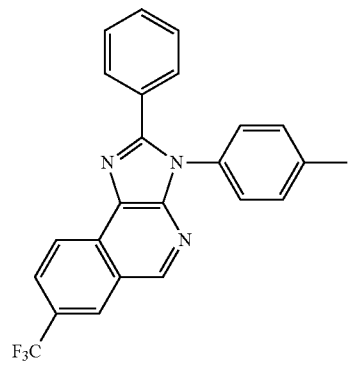
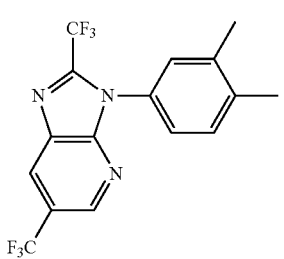
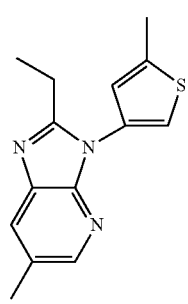
-continued
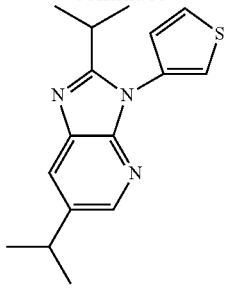
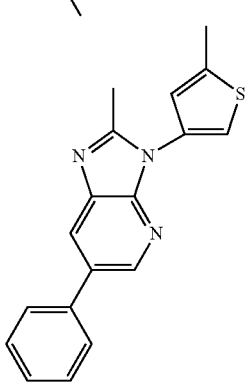
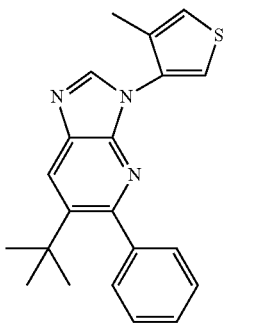
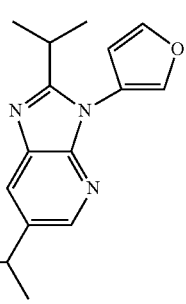

-continued
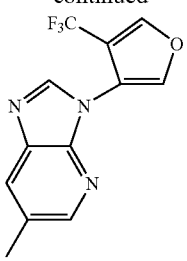
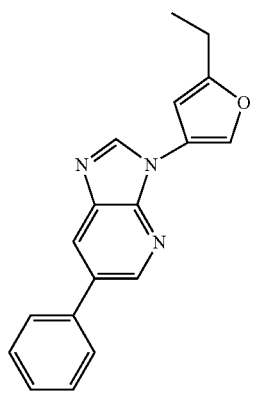
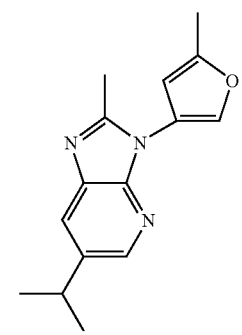
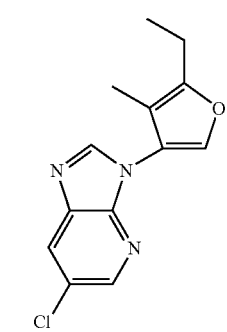
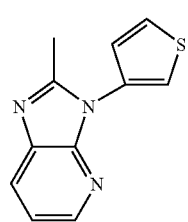
-continued
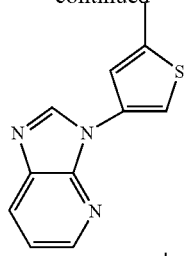
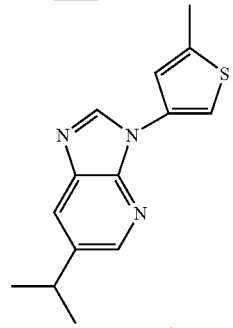
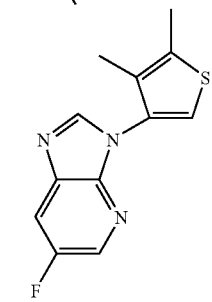
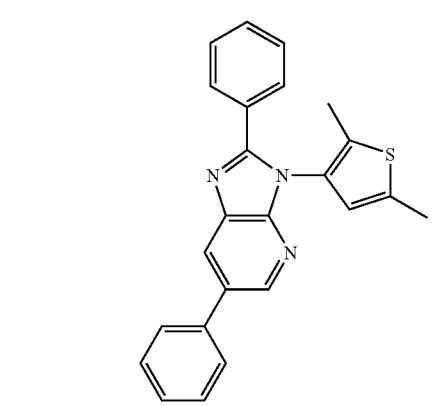
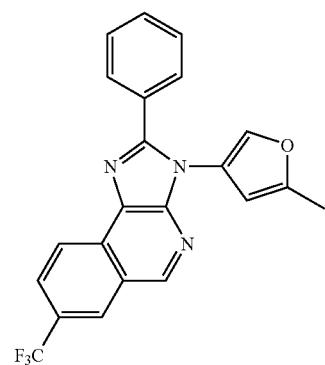

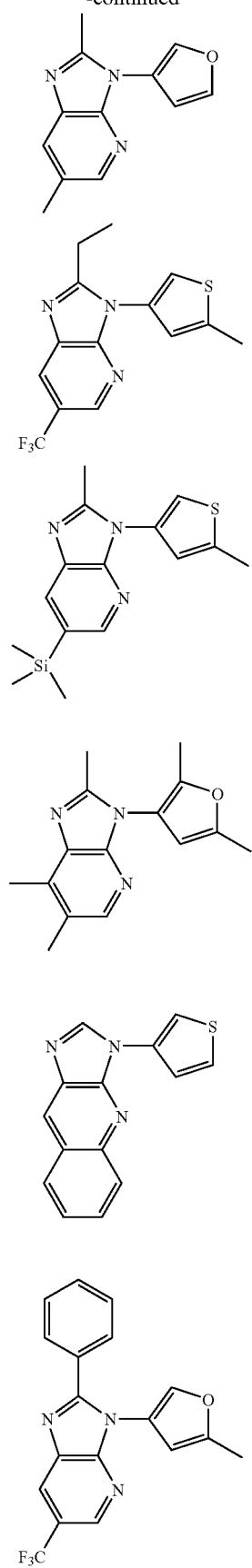
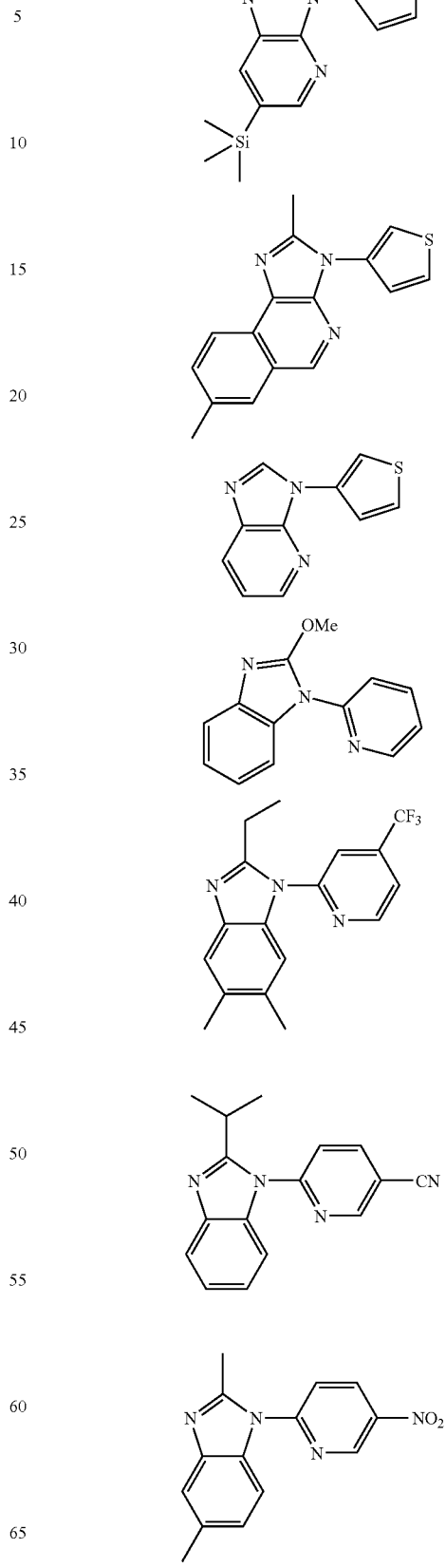

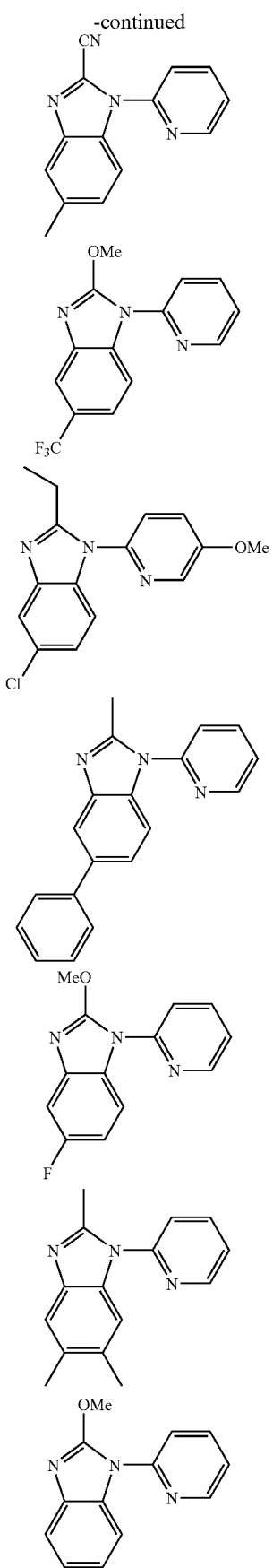
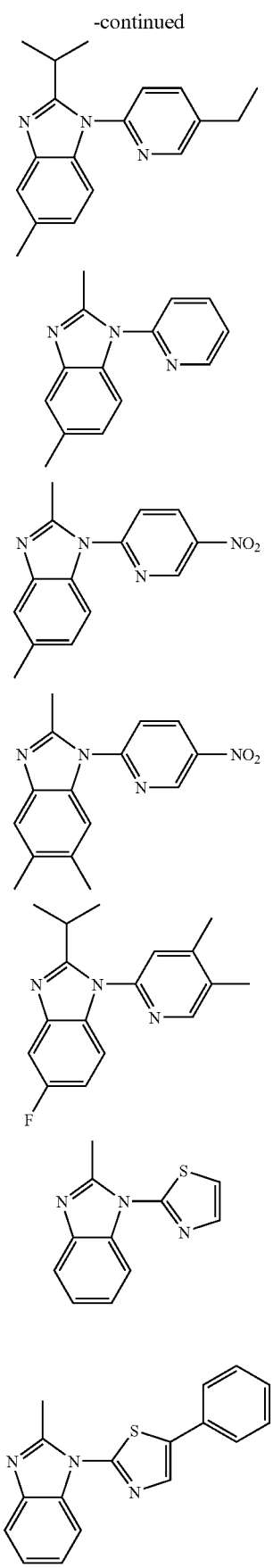

-continued
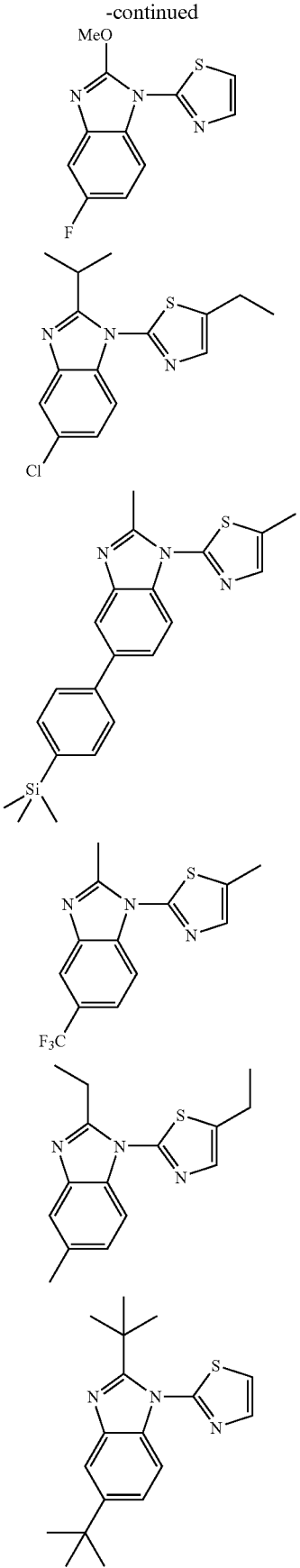
-continued
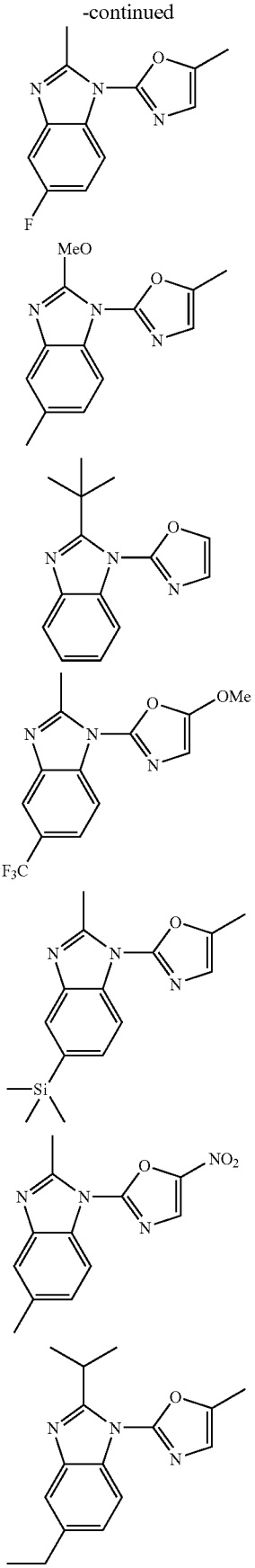

An $L^2$ ligand can change a small range of wavelength, and examples of the $L^2$ ligand are represented by the following Chemical Formulae 7:

[Chemical Formulae 9]

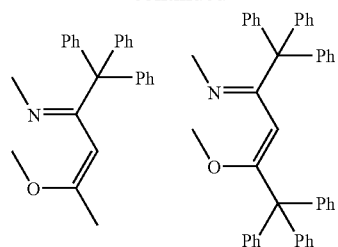
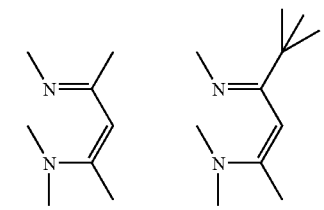
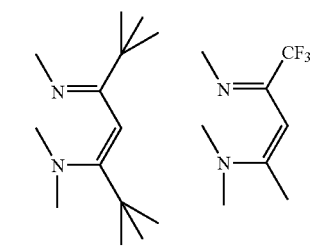
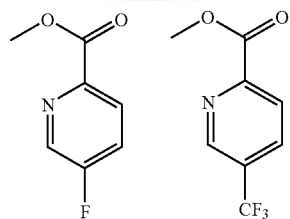
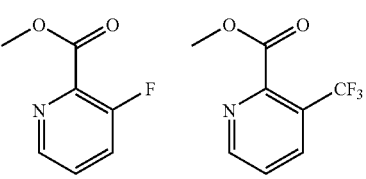
The transition metal compound represented by the above Chemical Formulae can be synthesized as follows. The following Reaction Schemes 1 and 2 show ligand syntheses, and Reaction Scheme 3 shows a metalation process.
[Reaction Scheme 1]
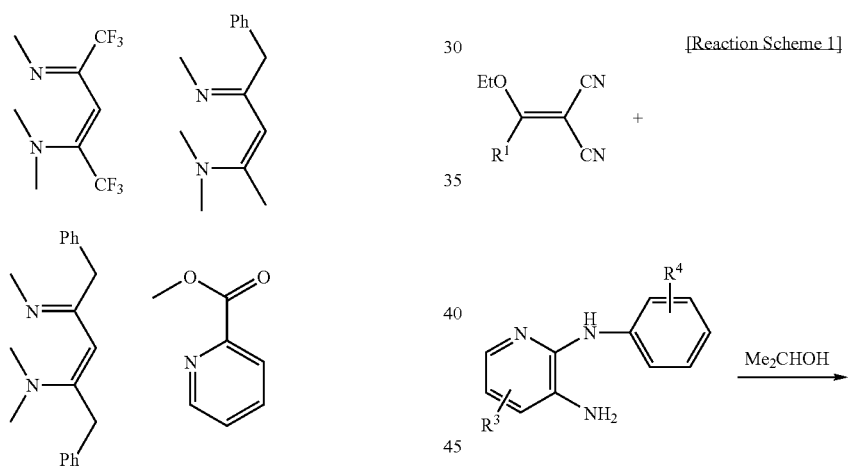
[Reaction Scheme 2]
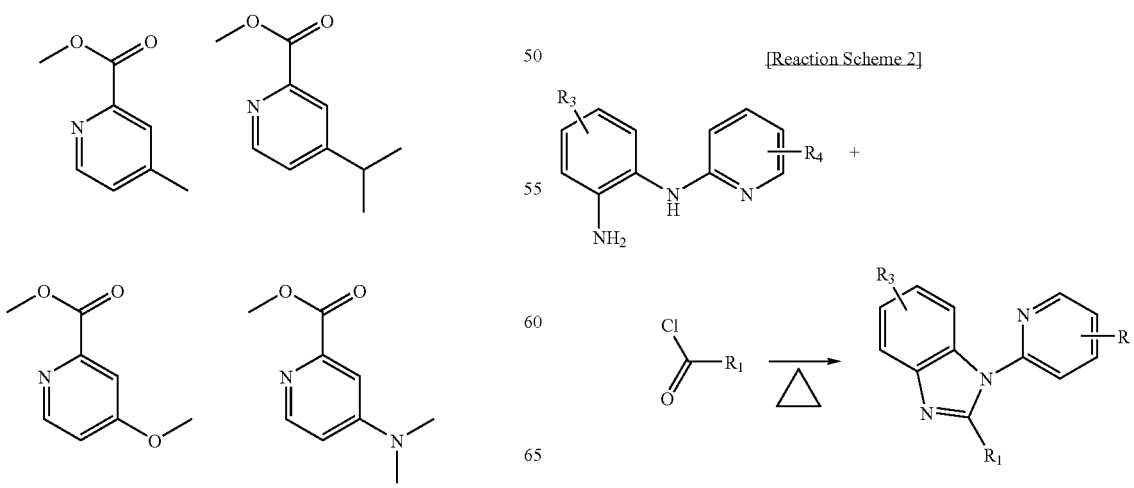

[Reaction Scheme 3]

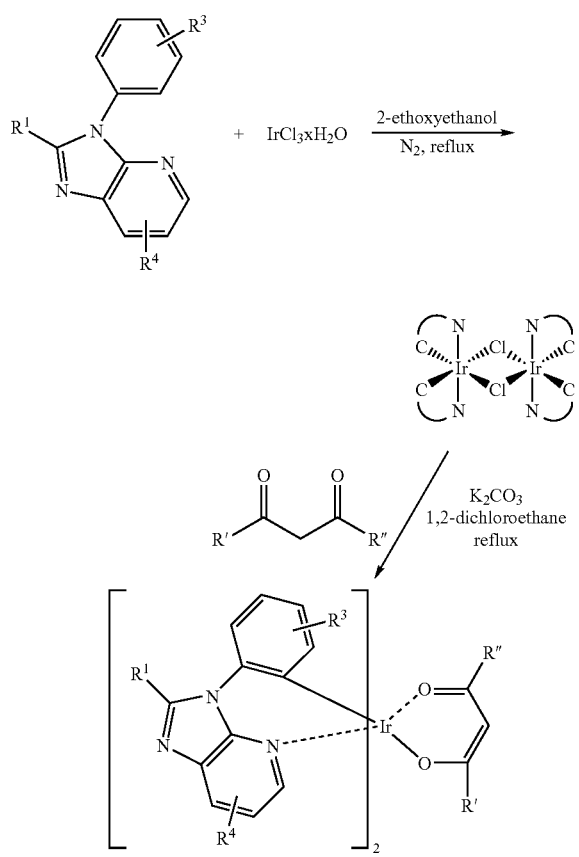

As shown in Reaction Scheme 3, the metalation process is as follows: a phenylene benzooxazole derivative and hydrated iridium trichloride are reacted under a nitrogen atmosphere to prepare a dimmer intermediate that includes two iridium metals sharing a Cl ligand, and then the intermediate is reacted with an auxiliary ligand in a solvent including a weak base to prepare transition metal compounds of Chemical Formulae 2 and 3.

THE EFFECT OF THE INVENTION

The phosphor material is applied to an organic electroluminescence device to increase the lifespan of a light emitting material, to increase the luminous efficiency, and to reduce concentration quenching. It can also be applied to display devices, displays, backlights, electron photographs, illumination sources, light sources, signs, signboards, interiors, and so on. Compared to a conventional fluorescent organic EL device having external quantum efficiency of less than 5%, power consumption can be significantly reduced. By introducing a substituent having steric hindrance, high efficiency can be maintained even at high doping concentration, and thereby the lifespan of a device increases. The compound of the present invention can be applied for medicals purposes, and to fluorescent brighteners, photographs, UV absorbents, laser dyes, dyes for a color filter, color conversion filters, and so on.

BEST MODE

The present invention can be specified by the following Examples. The Examples only illustrate the present invention and they do not limit the scope and range of the present invention, which is defined by the accompanying claims.

EXAMPLE 1

Compound 1: Synthesis of $(PhIP)_2Ir(acac)$

Synthesis of 3-phenylimidazo[4,5-b]pyridine (PhIP), 3-amino-2-phenylamino-pyridine 0.70 mol and ethoxymethylene malononitrile 2.56 mol were added to isopropanol 10 ml and refluxed for 6 hours. The solution was removed and purified by using column chromatography to thereby produce PhIP at a yield of 90%.

Synthesis of $(PhIP)_2Ir(Cl)_2Ir(PhIP)_2$, PIP 5 mmol and $IrCl_3 \times H_2O$ 10 mmol were dissolved in 2-ethoxyethanol 100 mL and refluxed for 24 hours under a nitrogen atmosphere. The solution was cooled down to room temperature, and 5% hydrochloric acid in a 200 mL aqueous solution was added to the solution for eduction, and the solution was then filtrated, rinsed with water and an ether solvent, and dried to thereby produce $(PhIP)_2Ir(Cl)_2Ir(PhIP)_2$ at a yield of 97%.

Synthesis of $(PhIP)_2Ir(acac)$: $(PhIP)_2Ir(Cl)_2Ir(PhIP)_2$ 5 mmol, 2,4-pentadione 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C. and filtrated. The filtrate solution was purified by using column chromatography to thereby produce $(PhIP)_2Ir(acac)$ at a yield of 88%.

EXAMPLE 2

Compound 2: Synthesis of $(PhIP)_2Ir(Facac)$

Synthesis of $(PhIP)_2Ir(Facac)$: $(PhIP)_2Ir(Cl)_2Ir(PhIP)_2$ 5 mmol, 1,1,1-trifluoropentane-2,4-dione 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C., and filtrated. The filtrate solution was purified by using column chromatography to thereby produce $(PhIP)_2Ir(Facac)$ at a yield of 85%.

EXAMPLE 3

Compound 3: Synthesis of $(PhIP)_2Ir(FacacF)$

Synthesis of $(PhIP)_2Ir(FacacF)$, $(PhIP)_2Ir(Cl)_2Ir(PhIP)_2$ 5 mmol, 1,1,1,5,5,5-hexafluoropentane-2,4-dione 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C., and filtrated. The filtrate solution was purified by using column chromatography to thereby produce $(PhIP)_2Ir(Facac)$ at a yield of 91%.

EXAMPLE 4

Compound 4: Synthesis of $(PhIP)_2Ir(pic)$

Synthesis of $(PhIP)_2Ir(pic)$: $(PhIP)_2Ir(Cl)_2Ir(PhIP)_2$ 5 mmol, picolinic acid 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C., and filtrated. The filtrate solution was purified by using column chromatography to thereby produce (PhIP)$_2$Ir(pic) at a yield of 94%.

EXAMPLE 5

Compound 5: Synthesis of (PhIP)$_2$Ir(Npic)

Synthesis of (PhIP)$_2$Ir(Npic): (PhIP)$_2$Ir(Cl)$_2$Ir(PhIP)$_2$ 5 mmol, 5-(dimethylamino)pyridine-2-carboxylic acid 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C., and filtrated. The filtrate solution was purified by using column chromatography to thereby produce (PhIP)$_2$Ir(Npic) at a yield of 92%.

EXAMPLE 6

Compound 6: Synthesis of (MPhIP)$_2$Ir(acac)

Synthesis of 2-methyl-3-phenylimidazo[4,5-b]pyridine (MPhIP), 3-amino-2-phenylamino-pyridine 0.70 mol and ethoxyethylydene malononitrile 2.56 mol were added to isopropanol 10 ml, and refluxed for 6 hours. The solution was removed and purified by using column chromatography to thereby produce MphIP at a yield of 88%.
Synthesis of (MPhIP)$_2$Ir(Cl)$_2$Ir(MPhIP)$_2$, MphIP 5 mmol and IrCl$_3$xH$_2$O 10 mmol were dissolved in 2-ethoxyethanol 100 mL, and refluxed for 24 hours under a nitrogen atmosphere. The solution was cooled down to room temperature, and 5% hydrochloric acid in a 200 mL aqueous solution was added thereto for eduction. The solution was then filtrated, rinsed with water and an ether solvent, and dried to thereby produce (MPhIP)$_2$Ir(Cl)$_2$Ir(MPhIP)$_2$ at a yield of 94%.
Synthesis of (MPhIP)$_2$Ir(acac): (MPhIP)$_2$Ir(Cl)$_2$Ir (MPhIP)$_2$ 5 mmol, 2,4-pentadione 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C. and filtrated. The filtrate solution was purified by using column chromatography to thereby produce (MPhIP)$_2$Ir(acac) at a yield of 90%.

EXAMPLE 7

Compound 7: Synthesis of (MPhIP)$_2$Ir(Facac)

Synthesis of (MPhIP)$_2$Ir(Facac): (MPhIP)$_2$Ir(Cl)$_2$Ir (MPhIP)$_2$ 5 mmol, 1,1,1-trifluoropentane-2,4-dione 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C., and filtrated. The filtrate solution was purified by using column chromatography to thereby produce (MPhIP)$_2$Ir(Facac) at a yield of 87%.

EXAMPLE 8

Compound 8: Synthesis of (MPhIP)$_2$Ir(FacacF)

Synthesis of (MPhIP)$_2$Ir(FacacF): (MPhIP)$_2$Ir(Cl)$_2$Ir (MPhIP)$_2$ 5 mmol, 1,1,1,5,5,5-hexafluoropentane-2,4-dione 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C., and filtrated. The filtrate solution was purified by using column chromatography to thereby produce (MPhIP)$_2$Ir(FacacF) at a yield of 90%.

EXAMPLE 9

Compound 9: Synthesis of (MPhIP)$_2$Ir(pic)

Synthesis of (MPhIP)$_2$Ir(pic): (MPhIP)$_2$Ir(Cl)$_2$Ir(MPhIP)$_2$ 5 mmol, picolinic acid 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C., and filtrated. The filtrate solution was purified by using column chromatography to thereby produce (MPhIP)$_2$Ir(pic) at a yield of 93%.

EXAMPLE 10

Compound 10: Synthesis of (MPhIP)$_2$Ir(Npic)

Synthesis of (MPhIP)$_2$Ir(Npic): (MPhIP)$_2$Ir(Cl)$_2$Ir (MPhIP)$_2$ 5 mmol, 5-(dimethylamino)pyridine-2-carboxylic acid 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C., and filtrated. The filtrate solution was purified by using column chromatography to thereby produce (MPhIP)$_2$Ir(Npic) at a yield of 92%.

EXAMPLE 11

Compound 11: Synthesis of 6-trimethylsilyl-3-phenylimidazo[4,5-b]pyridine (TMSPhIP)

For synthesis of 6-trimethylsilyl-3-phenylimidazo[4,5-b] pyridine (TMSPhIP), 5-trimethylsilyl-3-amino-2-phenylamino-pyridine 0.70 mol and ethoxymethylene malononitrile 2.56 mol were added to isopropanol 10 ml, and refluxed for 6 hours. The solution was removed and purified by using column chromatography to thereby produce TMSPhIP at a yield of 85%.
For synthesis of (TMSPhIP)$_2$Ir(Cl)$_2$Ir(TMSPhIP)$_2$, TMSPhIP 5 mmol and IrCl$_3$xH$_2$O 10 mmol were dissolved in 2-ethoxyethanol 100 mL, and refluxed for 24 hours under a nitrogen atmosphere. The solution was cooled down to room temperature, and 5% hydrochloric acid in a 200 mL aqueous solution was added thereto for eduction. The solution was then filtrated, rinsed with water and an ether solvent, and dried to thereby produce (TMSPhIP)$_2$Ir(Cl)$_2$Ir(TMSPhIP)$_2$ at a yield of 94%.
Synthesis of (TMSPhIP)$_2$Ir(acac): (TMSPhIP)$_2$Ir(Cl)$_2$Ir (TMSPhIP)$_2$ 5 mmol, 2,4-pentadione 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C., and filtrated. The filtrate solution was purified by using column chromatography to thereby produce (TMSPhIP)$_2$Ir(acac) at a yield of 87%.

EXAMPLE 12

Compound 12: Synthesis of (TMSPhIP)$_2$Ir(Facac)

Synthesis of (TMSPhIP)$_2$Ir(Facac): (TMSPhIP)$_2$Ir(Cl)$_2$Ir (TMSPhIP)$_2$ 5 mmol, 1,1,1-trifluoropentane-2,4-dione 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C., and filtrated. The filtrate solution was purified by using column chromatography to thereby produce (6-MPhIP)$_2$Ir(Facac) at a yield of 84%.

EXAMPLE 13

Compound 13: Synthesis of (TMSPhIP)$_2$Ir(FacacF)

Synthesis of (TMSPhIP)$_2$Ir(FacacF): (TMSPhIP)$_2$Ir(Cl)$_2$Ir(TMSPhIP)$_2$ 5 mmol, 1,1,1,5,5,5-hexafluoropentane-2,4-dione 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C., and filtrated. The filtrate solution was purified by using column chromatography to thereby produce (TMSPhIP)$_2$Ir(Facac) at a yield of 89%.

EXAMPLE 14

Compound 14: Synthesis of (TMSPhIP)$_2$Ir(pic)

Synthesis of (TMSPhIP)$_2$Ir(pic): (TMSPhIP)$_2$Ir(Cl)$_2$Ir(TMSPhIP)$_2$ 5 mmol, picolinic acid 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C., and filtrated. The filtrate solution was purified by using column chromatography to thereby produce (TMSPhIP)$_2$Ir(pic) at a yield of 91%.

EXAMPLE 15

Compound 15: Synthesis of (TMSPhIP)$_2$Ir(Npic)

Synthesis of (TMSPhIP)$_2$Ir(Npic): (TMSPhIP)$_2$Ir(Cl)$_2$Ir(TMSPhIP)$_2$ 5 mmol, 5-(dimethylamino)pyridine-2-carboxylic acid 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C., and filtrated. The filtrate solution was purified by using column chromatography to thereby produce (TMSPhIP)$_2$Ir(Npic) at a yield of 90%.

EXAMPLE 16

Compound 16: Synthesis of 6-trifluoromethyl-3-phenylimidazo[4,5-b]pyridine (TFPhIP)

synthesis of 6-trifluoromethyl-3-phenylimidazo[4,5-b]pyridine (TFPhIP): 5-trifluoromethyl-3-amino-2-phenylaminopyridine 0.70 mol and ethoxymethylene malononitrile 2.56 mol were added to isopropanol 10 ml, and refluxed for 6 hours. The solution was removed and purified by using column chromatography to thereby produce TFPhIP at a yield of 79%.

Synthesis of (TFPhIP)$_2$Ir(Cl)$_2$Ir(TFPhIP)$_2$, TFPhIP 5 mmol and IrCl$_3$×H$_2$O 10 mmol were dissolved in 2-ethoxyethanol 100 mL, and refluxed for 24 hours under a nitrogen atmosphere. The solution was cooled down to room temperature, and 5% hydrochloric acid in a 200 mL aqueous solution was added thereto for eduction. The solution was then filtrated, rinsed with water and an ether solvent, and dried to thereby produce (TFPhIP)$_2$Ir(Cl)$_2$Ir(TFPhIP)$_2$ at a yield of 95%.

Synthesis of (TFPhIP)$_2$Ir(acac): (TFPhIP)$_2$Ir(Cl)$_2$Ir(TFPhIP)$_2$ 5 mmol, 2,4-pentadione 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C., and filtrated. The filtrate solution was purified by using column chromatography to thereby produce (TFPhIP)$_2$Ir(acac) at a yield of 87%.

EXAMPLE 17

Compound 17: Synthesis of (TFPhIP)$_2$Ir(Facac)

Synthesis of (TFPhIP)$_2$Ir(Facac): (TFPhIP)$_2$Ir(Cl)$_2$Ir(TFPhIP)$_2$ 5 mmol, 1,1,1-trifluoropentane-2,4-dione 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C., and filtrated. The filtrate solution was purified by using column chromatography to thereby produce (TFPhIP)$_2$Ir(Facac) at a yield of 89%.

EXAMPLE 18

Compound 18: Synthesis of (TFPhIP)$_2$Ir(FacacF)

Synthesis of (TFPhIP)$_2$Ir(FacacF): (TFPhIP)$_2$Ir(Cl)$_2$Ir(TFPhIP)$_2$ 5 mmol, 1,1,1,5,5,5-hexafluoropentane-2,4-dione 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C., and filtrated. The filtrate solution was purified by using column chromatography to thereby produce (TFPhIP)$_2$Ir(Facac) at a yield of 93%.

EXAMPLE 19

Compound 19: Synthesis of (TFPhIP)$_2$Ir(pic)

Synthesis of (TFPhIP)$_2$Ir(pic): (TFPhIP)$_2$Ir(Cl)$_2$Ir(TFPhIP)$_2$ 5 mmol, picolinic acid 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C., and filtrated. The filtrate solution was purified by using column chromatography to thereby produce (TFPhIP)$_2$Ir(pic) at a yield of 90%.

EXAMPLE 20

Compound 20: Synthesis of (TFPhIP)$_2$Ir(Npic)

Synthesis of (TFPhIP)$_2$Ir(Npic): (TFPhIP)$_2$Ir(Cl)$_2$Ir(TFPhIP)$_2$ 5 mmol, 5-(dimethylamino)pyridine-2-carboxylic acid 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C., and filtrated. The filtrate solution was purified by using column chromatography to thereby produce (TFPhIP)$_2$Ir(Npic) at a yield of 88%.

EXAMPLE 21

Compound 21: Synthesis of 2,5-dimethyl-1-(pyridi-2-nyl)benzoimidazole (DMPBI)

For synthesis of 2,5-dimethyl-1-(pyridi-2-nyl)benzoimidazole (DMPBI), 4-methyl-(pyridi-2-nyl)benzene-1,2-diamine 2.4 mole was added to toluene solution 50 ml, and then chlorideacetyl 2.4 mole was added to the solution while agitating the solution. The mixture was refluxed for 13 hours while removing water therefrom. The mixture was cooled down, dried, dissolved in ethylacetate, dried, and purified by using column chromatography to thereby produce DMPBI at a yield of 50%.

Synthesis of $(DMPBI)_2Ir(Cl)_2Ir(DMPBI)_2$, DMPBI 5 mmol and $IrCl_3 \times H_2O$ 10 mmol were dissolved in 2-ethoxyethanol 100 mL, and refluxed for 24 hours under a nitrogen atmosphere. The solution was cooled down to room temperature, and 5% hydrochloric acid in a 200 mL aqueous solution was added thereto for eduction. The solution was then filtrated, rinsed with water and an ether solvent, and dried to thereby produce $(DMPBI)_2Ir(Cl)_2Ir(DMPBI)_2$ at a yield of 94%.

Synthesis of $(DMPBI)_2Ir(acac)$: $(DMPBI)_2Ir(Cl)_2Ir(DMPBI)_2$ 5 mmol, 2,4-pentadione 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C. and filtrated. The filtrate solution was purified by using column chromatography to thereby produce $(DMPBI)_2Ir(acac)$ at a yield of 90%.

EXAMPLE 22

Compound 22: Synthesis of $(DMPBI)_2Ir(Facac)$

Synthesis of $(DMPBI)_2Ir(Facac)$: $(DMPBI)_2Ir(Cl)_2Ir(DMPBI)_2$ 5 mmol, 1,1,1-trifluoropentane-2,4-dione 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C. and filtrated. The filtrate solution was purified by using column chromatography to thereby produce $(DMPBI)_2Ir(Facac)$ at a yield of 88%.

EXAMPLE 23

Compound 23: Synthesis of $(DMPBI)_2Ir(FacacF)$

Synthesis of $(DMPBI)_2Ir(FacacF)$: $(DMPBI)_2Ir(Cl)_2Ir(DMPBI)_2$ 5 mmol, 1,1,1,5,5,5-hexafluoropentane-2,4-dione 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C. and filtrated. The filtrate solution was purified by using column chromatography to thereby produce $(DMPBI)_2Ir(Facac)$ at a yield of 89%.

EXAMPLE 24

Compound 24: Synthesis of $(DMPBI)_2Ir(pic)$

Synthesis of $(DMPBI)_2Ir(pic)$: $(DMPBI)_2Ir(Cl)_2Ir(DMPBI)_2$ 5 mmol, picolinic acid 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C. and filtrated. The filtrate solution was purified by using column chromatography to thereby produce $(DMPBI)_2Ir(pic)$ at a yield of 93%.

EXAMPLE 25

Compound 25: Synthesis of $(DMPBI)_2Ir(Npic)$

Synthesis of $(DMPBI)_2Ir(Npic)$: $(DMPBI)_2Ir(Cl)_2Ir(DMPBI)_2$ 5 mmol, 5-(dimethylamino)pyridine-2-carboxylic acid 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C. and filtrated. The filtrate solution was purified by using column chromatography to thereby produce $(DMPBI)_2Ir(Npic)$ at a yield of 88%.

EXAMPLE 26

Compound 26: Synthesis of 5-trifluoromethyl-2-methyl-1-(pyridi-2-nyl)benzoimidazole (TFMPBI)

For synthesis of 5-trifluoromethyl-2-methyl-1-(pyridi-2-nyl)benzoimidazole (TFMPBI), 2-amino-2-pyridyl-4-trifluoromethylaniline 2.4 mole was added to toluene solution 50 ml, and then chlorideacetyl 2.4 mole was added to the solution while agitating the solution. The mixture was refluxed for 13 hours while removing water therefrom. The solution was cooled down, dried, dissolved in ethylacetate, dried, and purified by using column chromatography to thereby produce TFMPBI at a yield of 47%.

Synthesis of $(TFMPBI)_2Ir(Cl)_2Ir(TFMPBI)_2$, TFMPBI 5 mmol and $IrCl_3 \times H_2O$ 10 mmol were dissolved in 2-ethoxyethanol 100 mL, and refluxed for 24 hours under a nitrogen atmosphere. The solution was cooled down to room temperature, and 5% hydrochloric acid in a 200 mL aqueous solution was added thereto for eduction. The solution was then filtrated, rinsed with water and an ether solvent, and dried to thereby produce $(TFMPBI)_2Ir(Cl)_2Ir(TFMPBI)_2$ at a yield of 92%.

Synthesis of $(TFMPBI)_2Ir(acac)$: $(TFMPBI)_2Ir(Cl)_2Ir(TFMPBI)_2$ 5 mmol, 2,4-pentadione 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C. and filtrated. The filtrate solution was purified by using column chromatography to thereby produce $(TFMPBI)_2Ir(acac)$ at a yield of 86%.

EXAMPLE 27

Compound 27: Synthesis of $(TFMPBI)_2Ir(Facac)$

Synthesis of $(TFMPBI)_2Ir(Facac)$: $(TFMPBI)_2Ir(Cl)_2Ir(TFMPBI)_2$ 5 mmol, 1,1,1-trifluoropentane-2,4-dione 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C. and filtrated. The filtrate solution was purified by using column chromatography to thereby produce $(TFMPBI)_2Ir(Facac)$ at a yield of 89%.

EXAMPLE 28

Compound 28: Synthesis of (TFMPBI)$_2$Ir(FacacF)

Synthesis of (TFMPBI)$_2$Ir(FacacF): (TFMPBI)$_2$Ir(Cl)$_2$Ir(TFMPBI)$_2$ 5 mmol, 1,1,1,5,5,5-hexafluoropentane-2,4-dione 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C. and filtrated. The filtrate solution was purified by using column chromatography to thereby produce (TFMPBI)$_2$Ir(Facac) at a yield of 90%.

EXAMPLE 29

Compound 29: Synthesis of (TFMPBI)$_2$Ir(pic)

Synthesis of (TFMPBI)$_2$Ir(pic): (TFMPBI)$_2$Ir(Cl)$_2$Ir(TFMPBI)$_2$ 5 mmol, picolinic acid 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C. and filtrated. The filtrate solution was purified by using column chromatography to thereby produce (TFMPBI)$_2$Ir(pic) at a yield of 92%.

EXAMPLE 30

Compound 30: Synthesis of (TFMPBI)$_2$Ir(Npic)

Synthesis of (TFMPBI)$_2$Ir(Npic): (TFMPBI)$_2$Ir(Cl)$_2$Ir(TFMPBI)$_2$ 5 mmol, 5-(dimethylamino)pyridine-2-carboxylic acid 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C. and filtrated. The filtrate solution was purified by using column chromatography to thereby produce (TFMPBI)$_2$Ir(Npic) at a yield of 90%.

EXAMPLE 31

Compound 31: Synthesis of 2-methyl-5-nitro-1-(pyridi-2-nyl)benzoimidazole (MNPBI)

For synthesis of 2-methyl-5-nitro-1-(pyridi-2-nyl)benzoimidazole (MNPBI), 2-(2-amino-4-nitroanylino)pyridine 2.4 mole was added to toluene solution 50 ml and then chlorideacetyl 2.4 mole was added to the solution while agitating the solution. The mixture was refluxed for 13 hours while removing water therefrom. The mixture was cooled down, dried, dissolved in ethylacetate, dried, and purified by using column chromatography to thereby produce MNPBI at a yield of 51%.

Synthesis of (MNPBI)$_2$Ir(Cl)$_2$Ir(MNPBI)$_2$, MNPBI 5 mmol and IrCl$_3$xH$_2$O 10 mmol were dissolved in 2-ethoxyethanol 100 mL, and refluxed for 24 hours under a nitrogen atmosphere. The solution was cooled down to room temperature, and 5% hydrochloric acid in a 200 mL aqueous solution was added thereto for eduction. The solution was then filtrated, rinsed with water and an ether solvent, and dried to thereby produce (MNPBI)$_2$Ir(Cl)$_2$Ir(MNPBI)$_2$ at a yield of 97%.

Synthesis of (MNPBI)$_2$Ir(acac): (MNPBI)$_2$Ir(Cl)$_2$Ir(MNPBI)$_2$ 5 mmol, 2,4-pentadione 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C. and filtrated. The filtrate solution was purified by using column chromatography to thereby produce (MNPBI)$_2$Ir(acac) at a yield of 90%.

EXAMPLE 32

Compound 32: Synthesis of (MNPBI)$_2$Ir(Facac)

Synthesis of (MNPBI)$_2$Ir(Facac): (MNPBI)$_2$Ir(Cl)$_2$Ir(MNPBI)$_2$ 5 mmol, 1,1,1-trifluoropentane-2,4-dione 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C. and filtrated. The filtrate solution was purified by using column chromatography to thereby produce (MNPBI)$_2$Ir(Facac) at a yield of 87%.

EXAMPLE 33

Compound 33: Synthesis of (MNPBI)$_2$Ir(FacacF)

Synthesis of (MNPBI)$_2$Ir(FacacF): (MNPBI)$_2$Ir(Cl)$_2$Ir(MNPBI)$_2$ 5 mmol, 1,1,1,5,5,5-hexafluoropentane-2,4-dione 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C. and filtrated. The filtrate solution was purified by using column chromatography to thereby produce (MNPBI)$_2$Ir(Facac) at a yield of 92%.

EXAMPLE 34

Compound 34: Synthesis of (MNPBI)$_2$Ir(pic)

Synthesis of (MNPBI)$_2$Ir(pic): (MNPBI)$_2$Ir(Cl)$_2$Ir(MNPBI)$_2$ 5 mmol, picolinic acid 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C. and filtrated. The filtrate solution was purified by using column chromatography to thereby produce (MNPBI)$_2$Ir(pic) at a yield of 90%.

EXAMPLE 35

Compound 35: Synthesis of (MNPBI)$_2$Ir(Npic)

Synthesis of (MNPBI)$_2$Ir(Npic): (MNPBI)$_2$Ir(Cl)$_2$Ir(MNPBI)$_2$ 5 mmol, 5-(dimethylamino)pyridine-2-carboxylic acid 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C. and filtrated. The filtrate solution was purified by using column chromatography to thereby produce (MNPBI)$_2$Ir(Npic) at a yield of 91%.

EXAMPLE 36

Compound 36: Synthesis of 2-methyl-5-trimethylsilyl-1-(pyridi-2-nyl)benzoimidazole (MTMSPBI)

For synthesis of 2-methyl-5-trimethylsilyl-1-(pyridi-2-nyl)benzoimidazole (MTMSPBI), 4-(trimethylsilyl)-(pyridi-2-nyl)benzene-1,2-diamine 2.4 mole was added to dimethylacetamide solution 50 ml, and chlorideacetyl 2.4 mole was added to the solution while agitating the solution. The mixture was refluxed for 13 hours while removing water. The mixture was cooled down, dried, dissolved in ethylacetate, dried, and purified by using column chromatography to thereby produce MTMSPBI at a yield of 53%.

Synthesis of (MTMSPBI)$_2$Ir(Cl)$_2$Ir(MTMSPBI)$_2$: MTMSPBI 5 mmol and IrCl$_3$×H$_2$O 10 mmol were dissolved in 2-ethoxyethanol 100 mL, and refluxed for 24 hours under a nitrogen atmosphere. The solution was cooled down to room temperature, and 5% hydrochloric acid in a 200 mL aqueous solution was added thereto for eduction. The solution was then filtered, rinsed with water and an ether solvent, and dried to thereby produce (MTMSPBI)$_2$Ir(Cl)$_2$Ir(MTMSPBI)$_2$ at a yield of 95%. Synthesis of (MTMSPBI)$_2$Ir(acac), (MTMSPBI)$_2$Ir(Cl)$_2$Ir(MTMSPBI)$_2$ 5 mmol, 2,4-pentadione 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C. and filtrated. The filtrate solution was purified by using column chromatography to thereby produce (MTMSPBI)$_2$Ir(acac) at a yield of 91%.

EXAMPLE 37

Compound 37: Synthesis of (MTMSPBI)$_2$Ir(Facac)

Synthesis of (MTMSPBI)$_2$Ir(Facac): (MTMSPBI)$_2$Ir(Cl)$_2$Ir(MTMSPBI)$_2$ 5 mmol, 1,1,1-trifluoropentane-2,4-dione 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C. and filtrated. The filtrate solution was purified by using column chromatography to thereby produce (MTMSPBI)$_2$Ir(Facac) at a yield of 88%.

EXAMPLE 38

Compound 38: Synthesis of (MTMSPBI)$_2$Ir(FacacF)

Synthesis of (MTMSPBI)$_2$Ir(FacacF): (MTMSPBI)$_2$Ir(Cl)$_2$Ir(MTMSPBI)$_2$ 5 mmol, 1,1,1,5,5,5-hexafluoropentane-2,4-dione 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C. and filtrated. The filtrate solution was purified by using column chromatography to thereby produce (MTMSPBI)$_2$Ir(Facac) at a yield of 91%.

EXAMPLE 39

Compound 39: Synthesis of (MTMSPBI)$_2$Ir(pic)

Synthesis of (MTMSPBI)$_2$Ir(pic): (MTMSPBI)$_2$Ir(Cl)$_2$Ir(MTMSPBI)$_2$ 5 mmol, picolinic acid 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C. and filtrated. The filtrate solution was purified by using column chromatography to thereby produce (MTMSPBI)$_2$Ir(pic) at a yield of 90%.

EXAMPLE 40

Compound 40: Synthesis of (MTMSPBI)$_2$Ir(Npic)

Synthesis of (MTMSPBI)$_2$Ir(Npic), (MTMSPBI)$_2$Ir(Cl)$_2$Ir(MTMSPBI)$_2$ 5 mmol, 5-(dimethylamino)pyridine-2-carboxylic acid 25 mmol, and potassium carbonate 50 mmol were mixed in 1,2-dichloroethane 100 mL, and refluxed for 24 hours under a nitrogen atmosphere. After the reaction was complete, the solution was cooled down to about 50° C. and filtrated. The filtrate solution was purified by using column chromatography to thereby produce (MTMSPBI)$_2$Ir(Npic) at a yield of 92%.

PL spectra of the above chemical compounds were acquired and the results are presented in the following Table 1.

TABLE 1

| Compound | Yield | PL (nm) |
| --- | --- | --- |
| compound 1 | 91 | 551 |
| compound 2 | 87 | 549 |
| compound 3 | 92 | 545 |
| compound 4 | 90 | 547 |
| compound 5 | 89 | 545 |
| compound 6 | 90 | 553 |
| compound 7 | 89 | 551 |
| compound 8 | 87 | 549 |
| compound 9 | 88 | 550 |
| compound 10 | 88 | 547 |
| compound 11 | 91 | 549 |
| compound 12 | 92 | 547 |
| compound 13 | 93 | 544 |
| compound 14 | 88 | 544 |
| compound 15 | 87 | 542 |
| compound 16 | 87 | 558 |
| compound 17 | 86 | 555 |
| compound 18 | 85 | 552 |
| compound 19 | 86 | 554 |
| compound 20 | 87 | 551 |
| compound 21 | 88 | 591 |
| compound 22 | 86 | 589 |
| compound 23 | 85 | 585 |
| compound 24 | 86 | 586 |
| compound 25 | 87 | 584 |
| compound 26 | 91 | 588 |
| compound 27 | 90 | 585 |
| compound 28 | 93 | 580 |
| compound 29 | 92 | 584 |
| compound 30 | 90 | 578 |
| compound 31 | 93 | 590 |
| compound 32 | 90 | 587 |
| compound 33 | 89 | 585 |
| compound 34 | 88 | 589 |
| compound 35 | 87 | 583 |
| compound 36 | 94 | 593 |
| compound 37 | 92 | 590 |
| compound 38 | 90 | 587 |
| compound 39 | 91 | 588 |
| compound 40 | 89 | 584 |

EXAMPLE 41

For an anode, a 10 Ω/cm2 ITO substrate produced by the Corning Company was used. A hole injection layer was formed in a thickness of 60 nm by depositing IDE406 on top of the substrate under vacuum conditions. Subsequently, a hole transport layer was formed by depositing TPD chemical compound on top of the hole injection layer in a thickness of 30 nm under vacuum conditions. A light emitting layer was formed in a thickness of 20 nm by depositing a transition metal compound on top of the hole transport layer under vacuum conditions.

Subsequently, an HBL layer was formed in a thickness of 5 nm by depositing BCP on top of the light emitting layer under vacuum conditions. An electron transport layer (ETL) was formed in a thickness of 20 nm by depositing Alq3 on top of the light emitting layer under vacuum conditions. An organic electroluminescence device was completed by sequentially depositing LiF 1 nm and Al 300 nm on top of the electron transport layer in a vacuum condition to thereby form a LiF/Al electrode.

The luminance, color coordinates and efficiency of the organic electroluminescence device prepared according to Example 41 were measured.

As a result of the measurement, it can be confirmed that the organic electroluminescence device can be operated at a low voltage and implements high efficiency indicating that the metallic compound as an organic electro-luminescence material has excellent characteristics.

Simple modifications and alternations of the present invention can be easily made by the ordinary skilled person in the art within the spirit and scope of the appended claims.

The invention claimed is:

1. A metallic compound represented by the following Chemical Formula 1:

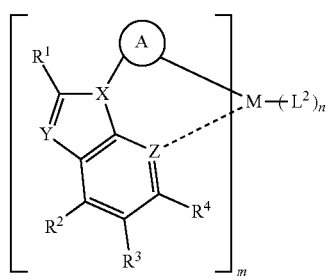

[Chemical Formula 1]

wherein:

M is Ir, Pt, Rh, Re, or Os, m is 2 or 3 and n is 0 or 1, where the sum of m and n is 3 provided that the sum of m and n is 2 when M is Pt, X, Y, and Z are the same or different and is N or P, and

is represented by any one selected from the following Chemical Formulae 3:

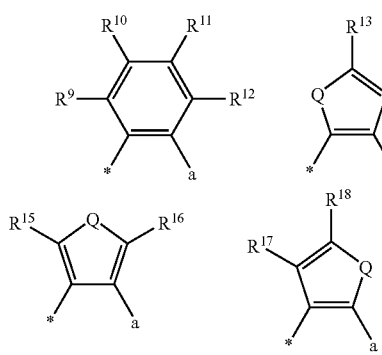

[Chemical Formulae 3]

wherein, in the above Chemical Formulae 3, Q is O, S, or Se, * denotes a portion that is covalently bound with X, and the transition metal M of the above Chemical Formula 1 forms a complex compound while bound with a portion denoted as "a" of the above Chemical Formulae 3 by a covalent bond and bound with Z of the Chemical Formula 1 by a coordination bond, $R^2$ to $R^4$ are the same or different, and are hydrogen, a C1 to C20 alkyl, an aryl, a cycloalkyl, a halogen, a linear or branched substituent including at least one halogen, a linear or branched substituent including at least one heteroatom, carbonyl, vinyl, or acetylenyl, or form a cycle, $R^9$ is hydrogen, $R^{10}$ is hydrogen, methyl, phenyl, $CF_3$, or forms a cycle with $R^{11}$, $R^{11}$ is hydrogen, methyl, forms a cycle with $R^{10}$, $R^{12}$ is hydrogen, $R^{13}$ to $R^{16}$ are each independently hydrogen or methyl, $R^{17}$ is hydrogen, methyl, or $CF_3$, $R^{18}$ is hydrogen, methyl, or ethyl, $R^1$ is hydrogen, a C1 to C7 alkyl excluding an aromatic cyclic substituent, a cycloalkyl, a halogen, a linear or branched substituent including at least one halogen, or a linear or branched substituent including at least one heteroatom, and $L^2$ is represented by the following Chemical Formulae 5, 6, or 7,

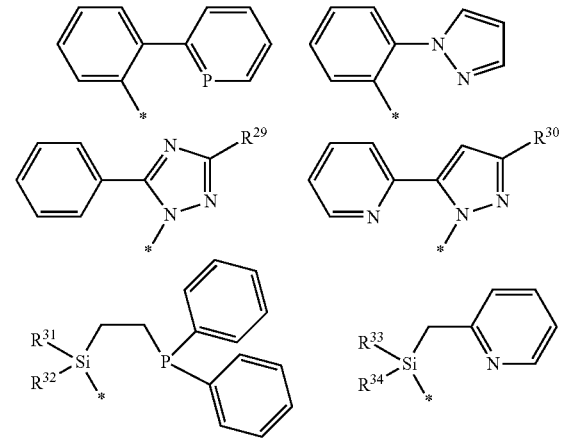

[Chemical Formulae 5]

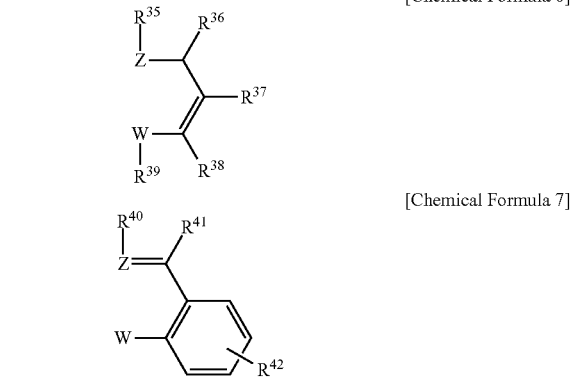

[Chemical Formula 6]

[Chemical Formula 7]

wherein, in the above Chemical Formula 1, M forms a complex compound by a covalent bond with a portion denoted as * in the above Chemical Formulae 5, and a coordination bond with an adjacent N or P, Z and W in the above Chemical Formulae 6 and 7 are the same or different and are a heteroatom selected from the group consisting of O, N, S, and P, and $R^{29}$-$R^{42}$ in the Chemical Formulae 5, 6, and 7 are the same or different, and are hydrogen, a C1 to C20 alkyl, an aryl, a cycloalkyl, a halogen, a linear or branched substituent including at least one halogen, a linear or branched substituent including at least one heteroatom, carbonyl, vinyl, or acetylenyl, or form a cycle.

2. A metallic compound represented by the following Chemical Formula 2:

[Chemical Formula 2]

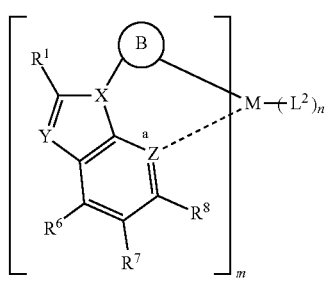

wherein:

M is Ir, Pt, Rh, Re, or Os, m is 2 or 3 and n is 0 or 1, where the sum of m and n is 3, provided that the sum of m and n is 2 when M is Pt, X, and Y are the same or different and is N or P,

is represented by any one selected from the following Chemical Formulae 4:

[Chemical Formulae 4]

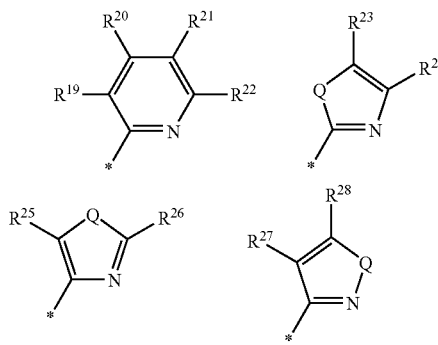

wherein, in the above Chemical Formula 4, Q is O, S, or Se,
* denotes a portion that is covalently bound with X, and the transition metal M of the above Chemical Formula 2 forms a complex compound while bound with N of the Chemical Formulae 4 by a coordination bond and bound with a portion denoted as "a" of the above Chemical Formula 2 by a covalent bond, $R^6$ to $R^8$ are the same or different, and are hydrogen, a C1 to C20 alkyl, an aryl, a cycloalkyl, a halogen, a linear or branched substituent including at least one halogen, a linear or branched substituent including at least one heteroatom, carbonyl, vinyl, or acetylenyl, or form a cycle, $R^{19}$, $R^{22}$, and $R^{24}$ to $R^{28}$ are hydrogen, $R^{20}$ is hydrogen, methyl, or $CF_3$, $R^{21}$ is hydrogen, methyl, —$NO_2$, —$OCH_3$, or —CN, $R^{23}$ is hydrogen, methyl, ethyl, phenyl, —$NO_2$, or —$OCH_3$, $R^5$ is hydrogen, a C1 to C7 alkyl excluding an aromatic cyclic substituent, a cycloalkyl, a halogen, a linear or branched substituent including at least one halogen, or a linear or branched substituent including at least one heteroatom, and $L^2$ is represented by the following Chemical Formulae 5, 6, and 7:

[Chemical Formulae 5]

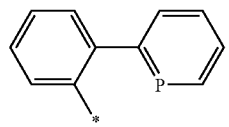

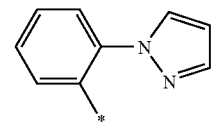

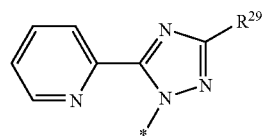

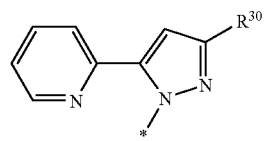

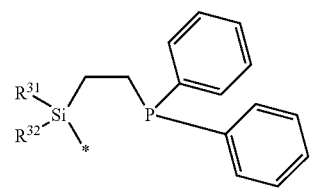

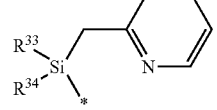

[Chemical Formulae 6]

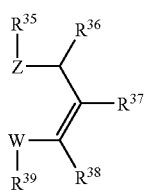

[Chemical Formulae 7]

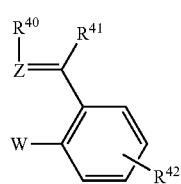

wherein, in the above Chemical Formula 2, M forms a complex compound by a covalent bond with a portion denoted as * in the above Chemical Formulae 5, and a coordination bond with an adjacent N or P, Z and W in the above Chemical Formulae 6 and 7 are the same or different and a heteroatom selected from the group consisting of O, N, S, and P, and $R^{29}$-$R^{42}$ in the Chemical Formulae 5, 6, and 7 are the same or different, and are hydrogen, a C1 to C20 alkyl, an aryl, a cycloalkyl, a halogen, a linear or branched substituent including at least one halogen, a linear or branched substituent including at least one heteroatom, carbonyl, vinyl, or acetylenyl, or form a cycle.

3. An organic electroluminescence device comprising the metallic compound according to claim 1.

4. An organic electroluminescence device comprising the metallic compound according to claim 2.

* * * * *